US011369506B2

(12) United States Patent
Thorgilsdottir et al.

(10) Patent No.: US 11,369,506 B2
(45) Date of Patent: *Jun. 28, 2022

(54) CERVICAL COLLAR HAVING HEIGHT AND CIRCUMFERENTIAL ADJUSTMENT

(71) Applicant: Ossur hf, Reykjavik (IS)

(72) Inventors: Thora Thorgilsdottir, Reykjavik (IS); Arni Thor Ingimundarson, Foothill Ranch, CA (US)

(73) Assignee: OSSUR HF, Reykjavik (IS)

( * ) Notice: Subject to any disclaimer, the term of this patent is extended or adjusted under 35 U.S.C. 154(b) by 378 days.

This patent is subject to a terminal disclaimer.

(21) Appl. No.: 16/400,449

(22) Filed: May 1, 2019

(65) Prior Publication Data

US 2019/0254860 A1 Aug. 22, 2019

Related U.S. Application Data

(63) Continuation of application No. 12/851,955, filed on Aug. 6, 2010, now Pat. No. 10,292,856.

(60) Provisional application No. 61/328,830, filed on Apr. 28, 2010, provisional application No. 61/232,559, filed on Aug. 10, 2009.

(51) Int. Cl.
*A61F 5/00* (2006.01)
*A61F 5/055* (2006.01)

(52) U.S. Cl.
CPC .................................... *A61F 5/055* (2013.01)

(58) Field of Classification Search
CPC ........ A61F 5/055; A61F 5/05883; A61F 5/05; A61F 5/3707; A61F 5/048; A61F 5/042; A61F 5/05891; A61F 5/058; A61F 5/00
See application file for complete search history.

(56) References Cited

U.S. PATENT DOCUMENTS

| | | | |
|---|---|---|---|
| 2,088,207 | A | 7/1937 | Kaiser |
| 2,102,069 | A | 12/1937 | Hanicke |
| 2,735,424 | A | 2/1953 | Benjamin |
| 2,791,999 | A | 5/1954 | Bustamante |
| 2,801,630 | A | 8/1957 | Moore |

(Continued)

FOREIGN PATENT DOCUMENTS

| | | |
|---|---|---|
| CN | 1646071 A | 7/2005 |
| CN | 2933343 Y | 8/2007 |

(Continued)

OTHER PUBLICATIONS

Levangie et al., "Joint Structure and Function: A Comprehensive Analysis", Fourth Edition, Chapter 4: The Vertebral Column, 2005 F.A. Davis Company, Philadelphia, PA, pp. 161-164.

(Continued)

*Primary Examiner* — Nictoria Hicks Fisher
(74) *Attorney, Agent, or Firm* — Workman Nydegger (57) ABSTRACT

A cervical collar has a front component formed from a compressible foam material and defines a recess constituting part of a tracheal opening. The collar also has a height adjustment mechanism secured to the front component which forms a substantially rigid border about the tracheal opening, and a sternum pad formed from a compressible foam material. The height adjustment mechanism selectively connects the front component to the sternum pad at a permanently locked position among a plurality of predefined distances.

18 Claims, 6 Drawing Sheets

(56) References Cited

U.S. PATENT DOCUMENTS

| | | |
|---|---|---|
| 2,806,471 A | 11/1957 | Breese |
| 2,818,063 A | 12/1957 | Smith et al. |
| 2,820,455 A | 1/1958 | Hall |
| 2,911,970 A | 11/1959 | Bartels |
| D188,302 S | 6/1960 | Monfardini |
| 3,024,784 A | 3/1962 | Monfardini |
| 3,027,894 A | 4/1962 | Moore |
| 3,042,027 A | 7/1962 | Monfardini |
| 3,050,052 A | 8/1962 | Grassl |
| 3,060,930 A | 10/1962 | Grassl |
| 3,075,521 A | 1/1963 | Grassl |
| 3,135,256 A | 6/1964 | Gruber |
| 3,177,869 A | 4/1965 | Bartels |
| D203,018 S | 11/1965 | Helferich |
| 3,285,243 A | 11/1966 | Yellin |
| 3,285,244 A | 11/1966 | Cottrell |
| 3,306,284 A | 2/1967 | McKinley |
| 3,313,297 A | 4/1967 | Applegate et al. |
| 3,320,950 A | 5/1967 | McElvenny |
| 3,504,667 A | 4/1970 | McFarlane |
| 3,512,523 A | 5/1970 | Barnett |
| 3,756,226 A | 9/1973 | Calabrese et al. |
| 3,916,884 A | 11/1975 | Attenburrow |
| 3,916,885 A | 11/1975 | Gaylord, Jr. |
| 4,099,523 A | 7/1978 | Lowrey |
| 4,173,973 A | 11/1979 | Hendricks |
| 4,205,667 A | 6/1980 | Gaylord, Jr. |
| 4,325,363 A | 4/1982 | Berkeley |
| 4,401,111 A | 8/1983 | Blackstone |
| 4,413,619 A | 11/1983 | Garth |
| D278,747 S | 5/1985 | Peach, Jr. |
| 4,520,801 A | 6/1985 | Lerman |
| 4,538,597 A | 9/1985 | Lerman |
| 4,562,833 A | 1/1986 | Pujals, Jr. |
| 4,582,051 A | 4/1986 | Greene et al. |
| 4,628,913 A | 12/1986 | Lerman |
| 4,643,174 A | 2/1987 | Horiuchi |
| 4,677,969 A | 7/1987 | Calabrese |
| 4,702,233 A | 10/1987 | Omicioli |
| 4,708,129 A | 11/1987 | Pujals, Jr. |
| 4,712,540 A | 12/1987 | Tucker et al. |
| 4,732,144 A | 3/1988 | Cunanan |
| 4,745,922 A | 5/1988 | Taylor |
| 4,827,915 A | 5/1989 | Gorsen |
| 4,854,306 A | 8/1989 | Pujals, Jr. |
| 4,886,052 A | 12/1989 | Calabrese |
| 4,940,043 A | 7/1990 | Burns et al. |
| 4,955,368 A | 9/1990 | Heimann |
| 4,987,891 A | 1/1991 | Gaylord, Jr. et al. |
| D314,623 S | 2/1991 | Calabrese et al. |
| 5,005,563 A | 4/1991 | Veale |
| 5,038,759 A | 8/1991 | Morgenstern |
| 5,058,572 A | 10/1991 | Schmid et al. |
| 5,060,637 A | 10/1991 | Schmid et al. |
| 5,097,824 A | 3/1992 | Garth |
| 5,156,588 A | 10/1992 | Marcune et al. |
| 5,180,361 A | 1/1993 | Moore et al. |
| 5,201,702 A | 4/1993 | Mars |
| 5,215,517 A | 6/1993 | Stevenson et al. |
| 5,230,698 A | 7/1993 | Garth |
| 5,275,581 A | 1/1994 | Bender |
| 5,302,170 A | 4/1994 | Tweardy |
| RE34,714 E | 8/1994 | Burns et al. |
| 5,346,461 A | 9/1994 | Heinz et al. |
| 5,366,438 A | 11/1994 | Martin, Sr. |
| 5,385,535 A | 1/1995 | McGuinness |
| 5,433,696 A | 7/1995 | Osti |
| 5,437,612 A | 8/1995 | Moore et al. |
| 5,437,617 A | 8/1995 | Heinz et al. |
| 5,445,602 A | 8/1995 | Grim et al. |
| D368,527 S | 4/1996 | Brooke |
| D369,660 S | 5/1996 | Myoga |
| 5,520,619 A | 5/1996 | Martin |
| RE35,290 E | 7/1996 | Druskoczi |
| 5,588,957 A | 12/1996 | Martin, Sr. |
| 5,593,382 A | 1/1997 | Rudy, Jr. et al. |
| 5,622,529 A * | 4/1997 | Calabrese ............... A61F 5/055 128/DIG. 23 |
| 5,624,387 A | 4/1997 | McGuinness |
| D379,232 S | 5/1997 | Brooke |
| 5,632,722 A | 5/1997 | Tweardy et al. |
| 5,688,229 A | 11/1997 | Bauer |
| 5,716,335 A | 2/1998 | Iglesias et al. |
| 5,728,054 A | 3/1998 | Martin |
| D393,718 S | 4/1998 | Traut et al. |
| 5,785,670 A | 7/1998 | Hiebert |
| 5,788,658 A | 8/1998 | Islava |
| 5,795,315 A | 8/1998 | Traut et al. |
| 5,797,713 A | 8/1998 | Tweardy et al. |
| 5,797,863 A | 8/1998 | Kohnke |
| RE35,940 E | 10/1998 | Heinz et al. |
| 5,865,773 A | 2/1999 | Koledin |
| 5,904,662 A | 5/1999 | Myoga |
| 5,934,599 A | 8/1999 | Hammerslag |
| 5,964,722 A | 10/1999 | Goralnik et al. |
| 5,976,098 A | 11/1999 | Sereboff |
| 5,993,403 A | 11/1999 | Martin |
| 6,027,467 A | 2/2000 | Nakamura et al. |
| 6,036,664 A | 3/2000 | Martin, Sr. et al. |
| D422,710 S | 4/2000 | Maynard |
| 6,045,522 A | 4/2000 | Grober |
| 6,045,523 A | 4/2000 | Donaldson |
| 6,050,965 A | 4/2000 | Pillai |
| 6,056,711 A | 5/2000 | Domamski et al. |
| 6,058,517 A | 5/2000 | Hartunian |
| RE36,745 E | 6/2000 | Rudy, Jr. et al. |
| 6,071,255 A | 6/2000 | Calabrese |
| 6,071,256 A | 6/2000 | Lam |
| 6,090,058 A | 7/2000 | Traut et al. |
| 6,165,146 A | 12/2000 | Giebeler |
| 6,183,501 B1 | 2/2001 | Latham |
| 6,202,953 B1 | 3/2001 | Hammerslag |
| 6,245,033 B1 | 6/2001 | Martin |
| 6,254,560 B1 | 7/2001 | Tweardy et al. |
| 6,308,345 B1 | 10/2001 | Williams, Jr. |
| 6,289,558 B1 | 11/2001 | Hammerslag |
| 6,315,746 B1 | 11/2001 | Garth et al. |
| 6,423,020 B1 | 7/2002 | Koledin |
| 6,458,090 B1 | 10/2002 | Walpin |
| 6,494,854 B1 | 12/2002 | Visness et al. |
| D475,139 S | 5/2003 | Myoga |
| 6,632,722 B2 | 10/2003 | Fujiwara et al. |
| 6,663,581 B1 | 12/2003 | Calabrese |
| 6,663,630 B2 | 12/2003 | Farley et al. |
| 6,726,643 B1 | 4/2004 | Martin |
| 6,733,469 B2 | 5/2004 | Miyaji et al. |
| 6,740,055 B2 | 5/2004 | Dominguez |
| 6,770,046 B2 | 8/2004 | Hansen |
| 6,872,188 B2 | 3/2005 | Caille et al. |
| 6,913,584 B2 | 7/2005 | Rudy, Jr. et al. |
| 6,921,376 B2 | 7/2005 | Tweardy et al. |
| 6,926,686 B2 | 8/2005 | Cheatham |
| 7,018,351 B1 | 3/2006 | Iglesias et al. |
| 7,041,073 B1 | 5/2006 | Patron |
| 7,070,573 B2 | 7/2006 | Axelsson |
| 7,090,652 B2 | 8/2006 | Santelli, Jr. |
| 7,090,653 B2 | 8/2006 | Moeller |
| 7,128,724 B2 | 10/2006 | Marsh |
| 7,141,031 B2 | 11/2006 | Garth et al. |
| 7,198,610 B2 | 4/2007 | Ingimundarson et al. |
| D542,919 S | 5/2007 | Leatt |
| 7,258,677 B2 | 8/2007 | Rudy, Jr. et al. |
| D552,742 S | 10/2007 | Leatt |
| 7,291,121 B2 | 11/2007 | Rudy, Jr. et al. |
| 7,297,127 B2 | 11/2007 | Lee et al. |
| 7,311,686 B1 | 12/2007 | Iglesias et al. |
| 7,371,221 B1 | 5/2008 | Baker |
| 7,371,222 B2 | 5/2008 | Heinz et al. |
| 7,399,288 B2 | 7/2008 | Chao |
| 7,442,176 B2 | 10/2008 | Cojbasic |
| D609,815 S | 2/2010 | Patterson |
| 7,674,234 B2 | 3/2010 | Calco et al. |
| D616,555 S | 5/2010 | Thorgilsdottir et al. |
| D616,996 S | 6/2010 | Thorgilsdottir et al. |

(56) References Cited

U.S. PATENT DOCUMENTS

| | | |
|---|---|---|
| D616,997 S | 6/2010 | Thorgilsdottir et al. |
| D617,907 S | 6/2010 | Waller |
| 7,815,585 B2 | 10/2010 | Vollbrecht |
| 7,846,117 B2 | 12/2010 | Leatt et al. |
| D631,167 S | 1/2011 | Leatt et al. |
| 7,878,995 B2 | 2/2011 | Harty |
| 7,896,827 B2 | 3/2011 | Ingimundarson et al. |
| 7,981,068 B2 | 7/2011 | Thorgilsdottir et al. |
| D643,978 S | 8/2011 | Abajo Alonso et al. |
| D644,331 S | 8/2011 | Sandhu |
| D644,332 S | 8/2011 | Sandhu |
| 7,992,261 B2 | 8/2011 | Hammerslag et al. |
| D647,623 S | 10/2011 | Thorgilsdottir et al. |
| D647,624 S | 10/2011 | Thorgilsdottir et al. |
| 8,038,635 B2 | 10/2011 | Dellanno |
| 8,038,636 B2 | 10/2011 | Thorgilsdottir et al. |
| D659,842 S | 5/2012 | Donaldson et al. |
| D662,597 S | 6/2012 | Chang |
| 8,216,167 B2 | 7/2012 | Garth et al. |
| D666,302 S | 8/2012 | Joseph |
| 8,257,292 B2 | 9/2012 | Linares |
| 8,545,423 B2 | 8/2013 | Patron |
| D692,568 S | 10/2013 | Chiang et al. |
| D693,014 S | 11/2013 | Chiang et al. |
| 8,679,044 B2 | 3/2014 | Thorgilsdottir et al. |
| 8,932,243 B2 | 1/2015 | Calabrese |
| 9,132,027 B2 | 9/2015 | Calco |
| D767,825 S | 9/2016 | Georgeson et al. |
| 9,713,546 B2 | 7/2017 | Thorsteinsdottir et al. |
| 10,292,856 B2 * | 5/2019 | Thorgilsdottir .......... A61F 5/055 |
| 10,675,173 B2 | 6/2020 | Thorsteinsdottir et al. |
| 2002/0138028 A1 | 9/2002 | Rudy, Jr. et al. |
| 2002/0156408 A1 | 10/2002 | Cheatham |
| 2002/0156409 A1 | 10/2002 | Lee et al. |
| 2002/0169401 A1 | 11/2002 | Walpin |
| 2002/0173737 A1 | 11/2002 | Miyaji et al. |
| 2003/0055367 A1 | 3/2003 | Dominguez |
| 2003/0060744 A1 | 3/2003 | Caille et al. |
| 2003/0181838 A1 | 9/2003 | Garth |
| 2004/0039318 A1 | 2/2004 | Santelli, Jr. |
| 2005/0101896 A1 | 5/2005 | Calabrese |
| 2007/0027418 A1 | 2/2007 | Calco et al. |
| 2007/0073203 A1 | 3/2007 | Moenning et al. |
| 2007/0270728 A1 | 11/2007 | Chao |
| 2009/0247918 A1 | 10/2009 | Patron |
| 2010/0137768 A1 | 6/2010 | Thorgilsdottir et al. |
| 2010/0268139 A1 | 10/2010 | Garth |
| 2010/0298748 A1 | 11/2010 | Rosenfeld et al. |
| 2011/0066094 A1 | 3/2011 | Thorgilsdottir et al. |
| 2011/0224591 A1 | 9/2011 | Thorgilsdottir et al. |
| 2012/0053499 A1 | 3/2012 | Donaldson et al. |
| 2012/0130295 A1 | 5/2012 | Haider |
| 2012/0165712 A1 | 6/2012 | Calabrese |
| 2013/0060179 A1 | 3/2013 | Modglin |
| 2013/0281899 A1 | 10/2013 | Suarez et al. |
| 2013/0281900 A1 | 10/2013 | Suarez et al. |
| 2013/0310722 A1 | 11/2013 | Thorsteinsdottir et al. |
| 2014/0012172 A1 | 1/2014 | Calco |
| 2014/0107551 A1 | 4/2014 | Modglin |
| 2014/0323938 A1 | 10/2014 | Suarez et al. |
| 2015/0216708 A1 | 8/2015 | Garth et al. |
| 2016/0008158 A1 | 1/2016 | Martin et al. |
| 2016/0287424 A1 | 10/2016 | Webster et al. |
| 2017/0246022 A1 | 8/2017 | Calco et al. |
| 2017/0252198 A1 | 9/2017 | Thorsteinsdottir et al. |
| 2018/0078400 A1 | 3/2018 | Hsu et al. |
| 2018/0078401 A1 | 3/2018 | Hsu et al. |
| 2020/0281754 A1 | 9/2020 | Thorsteinsdottir et al. |

FOREIGN PATENT DOCUMENTS

| | | | |
|---|---|---|---|
| CN | 201150587 Y | 11/2008 | |
| CN | 201602923 U | 10/2010 | |
| CN | 102227196 A | 10/2011 | |
| CN | 202015274 U | 10/2011 | |
| CN | 204655220 U | 9/2015 | |
| CN | 105120808 A | 12/2015 | |
| DE | 19547115 A1 | 6/1997 | |
| DE | 19849302 A1 | 4/2000 | |
| DE | 10057286 A1 | 5/2002 | |
| EP | 1738724 A1 | 1/2007 | |
| EP | 2653139 A1 | 10/2013 | |
| EP | 2886088 A1 | 6/2015 | |
| FR | 2814362 A1 | 3/2002 | |
| GB | 2165157 A | 4/1986 | |
| GB | 2453996 A | 4/2009 | |
| GB | 2453996 A * | 4/2009 | ............. A61F 5/055 |
| JP | 2007-330808 A | 12/2007 | |
| WO | 94/09728 A1 | 5/1994 | |
| WO | 95/22304 A1 | 8/1995 | |
| WO | 96/40018 A1 | 12/1996 | |
| WO | 9843568 A1 | 10/1998 | |
| WO | 2014102340 A1 | 7/2014 | |

OTHER PUBLICATIONS

Hsu et al., AAOS Atlas of Orthoses and Assistive Devices, Mosby, Elsevier Fourth Edition, 2008, Philadelphia, PA, p. 117-122.

Product Information Sheet, Philadelphia Tracheotomy Collar, obtained from www.ossur.com, prior to Aug. 6, 2010, 1 page.

Product Information Sheet, Platazote Sheets, WBC Industries, obtained from www.wbcindustries.com prior to Aug. 6, 2010, 2 pages.

"Range-of-Motion Restriction and Craniofacial Tissue-Interface Pressure From Four Cervical Collars", The Journal of Trauma Injury, Infection, and Critical Care, vol. 63, No. 5, Nov. 2007, pp. 1120-1126.

"Ossur Is Immobilization", www.ossur.com, 2008, pp. 1-16.

"Miami J Patient Care Handbook", www.ossur.com, 2010, pp. 1-16.

Jacobson et al. "Improving Practice Efforts to Reduce Occipital Pressure Ulcers", Journal of Nursing Care Quality, vol. 23, No. 3, 2008, pp. 283-288.

Bell et al. "Assessing Range of Motion to Evaluate the Adverse Effects of Ill-Fitting Cervical Orthoses", The Spine Journal, vol. 9, 2009, pp. 225-231.

Karason et al. "Evaluation of Clinical Efficacy and Safety of Cervical Trauma Collars: Differences in Immobilization, Effect on Jugular Venous Pressure and Patient Comfort", Scandinavian Journal of Trauma, Resuscitation and Emergency Medicine, 2014, pp. 1-7.

Product Brochure, "Capital Collar Enhanced", DeRoyal, 2014, 2 Pages.

Product Brochure, "Miami J Advanced by OSSUR", www.ossur.com, 2012, 4 Pages.

Product Brochure, "Miami J Cervical Collar", www.ossur.com, 1 Page.

Product Brochure, "Proglide Cervical Collar", OPTEC, www.optecusa.com, 1 Page.

Product Brochure, "Vista Upper Spine", Aspen Medical Products, 2015, 6 Pages.

Product Brochure, "Instructions for Use Eclipse Cervical Collar", VQ OrthoCare, 2015, 2 Pages.

Office Action from corresponding CN Application No. 201780057654.X, dated Oct. 29, 2020.

* cited by examiner

FIG. 16

CERVICAL COLLAR HAVING HEIGHT AND CIRCUMFERENTIAL ADJUSTMENT

CROSS REFERENCE TO RELATED APPLICATIONS

This application is a continuation of U.S. patent application Ser. No. 12/851,955 filed on Aug. 6, 2010, which claims the benefit of U.S. provisional patent application 61/232,559, filed on Aug. 10, 2009, and U.S. provisional patent application 61/328,830, filed on Apr. 28, 2010. This application incorporates in its entirety the disclosure of U.S. provisional applications, 61/232,559 and 61/328,830.

FIELD OF THE INVENTION

The invention generally relates to the field of orthopedic or prosthetic devices and more specifically to a cervical collar arranged to accommodate a variety of wearer sizes including height and circumferential width adjustment, improve patient comfort and adjust or set the collar for different medical indications.

BACKGROUND

Cervical collars are used in the treatment, stabilization, and therapy of cervical trauma. Some collars are intended to provide support for whiplash and other such injuries where support for the head and neck is needed. Other collars are intended for near complete immobilization of the head and neck, such as in an EMS pre-hospital setting.

There is often a rush to apply these collars onto the wearer due to the acute nature of cervical injuries. The collar must be selected to accommodate the wearer's size in a quick manner for effective stabilization and immobilization of the neck of the wearer.

Known cervical collars restrict spine flexion, extension and rotation to promote wearer recovery. Such known collars also include a trachea opening allowing for healthcare clinicians the ability to perform quick carotid pulse monitoring and emergency tracheotomies while providing cervical immobilization.

A drawback to known collars is that they are individually sized for a variety of standard wearer sizes. It follows that there is a need to store many different sized collars in inventory which significantly adds to the cost for using such collars. In the event there is an emergency, and the proper sized collar is not available, the caregiver is given little option other than to apply a poorly fitting collar on the wearer since many known collars provide minimal size adjustment.

Proper sizing is critical for wearer immobilization and comfort. While there are a variety of different standard sizes, the wearer may have dimensions which fall outside of the standard sizes, and thus wear a poorly fitting collar that insufficiently immobilizes the wearer's neck. Such poor fitting may also cause significant discomfort to the wearer.

Over time, swelling of the wearer's neck may reduce which further complicates the sizing of the collar. This may lead to the need for disposing the initially selected collar and replacing it with a new collar. This may lead to waste and an increase in cost.

When sizing a cervical collar, the first notable dimension concerns the height. The height is measured by the vertical distance from the tip of the chin to the sternum; the other key dimension concerns the circumference of the wearer's neck.

In addition to sizing, proper application of the collar is necessary for immobilization and wearer comfort. A typical collar consists of front and rear components which are packaged as a set according to the size of the wearer.

When applying a collar to the wearer, the rear component of the collar is applied to the back of the wearer's neck. Once the back wearer is positioned appropriately, the front component of the collar is positioned against the front or anterior portion of the neck so that a chin support is placed against the chin. The front component is centered to secure neutral alignment. The front component overlaps the rear component to ensure effective immobilization and comfort. Straps are then tightened to the collar with a bilateral adjustment which secures the wearer's cervical region in neutral alignment.

SUMMARY

The present invention provides a cervical collar having height and circumferential adjustment in order to accommodate a wide variety of sizes of different wearers and to accommodate size changes caused by increased or decreased swelling of the affected anatomical portions of the wearers.

According to an embodiment of the cervical collar, the cervical collar includes a front component formed from a compressible foam material and defines a recess forming a portion of a tracheal opening, and a height adjustment mechanism secured to the front component and forming a rigid border to the tracheal opening. The height adjustment mechanism selectively connects the front component to a sternum pad at a permanently locked position among a plurality of predefined distances.

In accordance with this disclosure, "permanently locked" is defined as once the height adjustment mechanism is placed at a particular height setting among a plurality of predefined height settings, it can be permanently locked at such height setting; no further adjustment of the height of the collar is possible.

The cervical collar may include a rear component connecting to the front component, and have a plurality of lateral breakaway sections formed at side portions of the rear component. The breakaway sections are arranged to be removed without the benefit of a tool such that removal of one of the breakaway sections reduces a circumference of the collar formed by the combination of the front and rear components. The rear component may be resiliently contoured in a generally arcuate shape such that the front and rear components form from their arcuate shapes a circumferential configuration for securing about a wearer's neck.

The rear component may be formed from compressible foam, and include a reinforcement support arranged to support a wearer's spine and an elongate strap arranged to secure to the front component. A rear gap may be formed between a top portion of the reinforcement support and the rear component. This gap may allow for expansion of the wearer's neck without reducing the circumference of the collar.

In an embodiment of the height adjustment mechanism, the height adjustment mechanism includes an upper part secured to the front component, and a lower part secured to the sternum pad and bordering the lower portion of the tracheal opening. The lower part defines a first arm bordering a side of the tracheal opening and the upper part defines a retainer through which the arm slides. The retainer is only located at a bottom portion of the upper part, such that when inserted through the retainer, the arm extends past the retainer and toward a top portion of the upper part. The location of the retainer permits the arms to be securely connected to the upper part at the first point of engagement as well as throughout the length of the height adjustment of the collar.

The first retainer may form a window and the arm may form a series of location identifiers representing a plurality of distance settings of the front component relative to the sternum pad. Preferably, an individual one of the location identifiers may be arranged to be placed in register with the window when the arm is inserted into the retainer. A lip may be formed around each of the location identifiers, a lip corresponding to the location identifier in the window engaging edges of the window. This window allows for the clinician to quickly compare the height of the lower part relative to the upper part, assuring that both sides are positioned at the same height.

According to a variation of the cervical collar, the upper part forms an elongate recess arranged to accommodate the arm. A variable gap is defined between the uppermost section of the arm relative to the recess thereby permitting some adjustment of the uppermost section of the arm relative to the upper part.

In order to permanently lock the upper part relative to the lower part of the height adjustment mechanism, according to an embodiment of the height adjustment mechanism, the lower part includes a pin fixedly securable to at least one of a series of locking elements formed along the upper part. The locking element into which the pin is secured corresponds to the location identifier located in the window.

In a variation of the lower part, the lower part forms a central tab connected to the sternum pad. The central tab has a living hinge adapted to bias the tab and sternum pad to a remainder of the lower part. Also, the lower part may form a side tab corresponding to the arm, and the side tab may have a living hinge adapted to bias the side tab relative to the sternum pad.

These and other features, aspects, and advantages of the present invention will become better understood with regard to the following description, appended claims, and accompanying drawings.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary configurations of a cervical collar having height and circumferential adjustment and the respective components thereof, and in no way limit the structures or configurations of a cervical collar and components thereof according to the present disclosure.

DETAILED DESCRIPTION OF VARIOUS EMBODIMENTS

A. Environment and Context

Embodiments of an orthopedic device are provided for use in stabilizing and supporting anatomical portions of a wearer, for example, the neck and head of a wearer.

Although the embodiments of the disclosure are adapted for supporting and stabilizing anatomical portions of a large number of wearers having various anatomical shapes and sizes, the embodiments of the disclosure may also be dimensioned to accommodate different types, shapes and sizes of anatomical portions.

For ease of understanding the disclosed embodiments of an orthopedic device, the front or anterior, and rear or posterior portions of the orthopedic device are described independently. It will be recognized that the anterior and posterior portions of the orthopedic device function together to form a supporting and stabilizing collar that encompasses the anatomical portions of the wearer.

The term "posterior" also has its ordinary meaning and refers to a location that is behind or to the rear of another location. Lastly, the term "anterior" has its ordinary meaning and refers to a location that is ahead of or to the front of another location.

The terms "rigid," "semi-rigid," "flexible," and "compressible" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. As for the term "semi-rigid," this term is used to connote properties of support members or shells that provide support and are free-standing; however such support members or shells may have some degree of flexibility or resiliency.

On the other hand, the term "flexible" is intended to denote that features are capable of repeated bending such that the features may be bent into retained shapes or the features do not retain a general shape, but continuously deform when force is applied. The term "compressible" is used to qualify such structural features as being capable of being reduced in size or volume due to the exertion of force applied to the structural feature.

B. Various Embodiments of Cervical Collar

The cervical collar described herein includes front and rear components constructed from flexible and compressible foam. Anterior and posterior rigid plastic reinforcement supports are applied to the front and rear components, respectively, to limit movement of the front and rear components. Adjustable hook and loop fasteners couple the front and rear components to one another, and secure to the anterior and posterior reinforcement supports.

Figure 1:
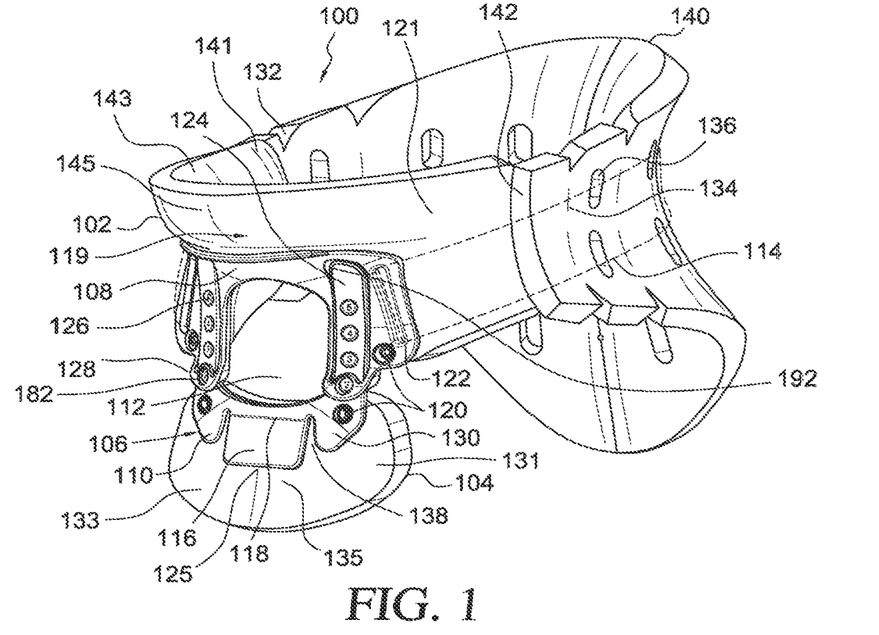
FIG. 1 is a front perspective view of an embodiment of the cervical collar.
Figure 2:
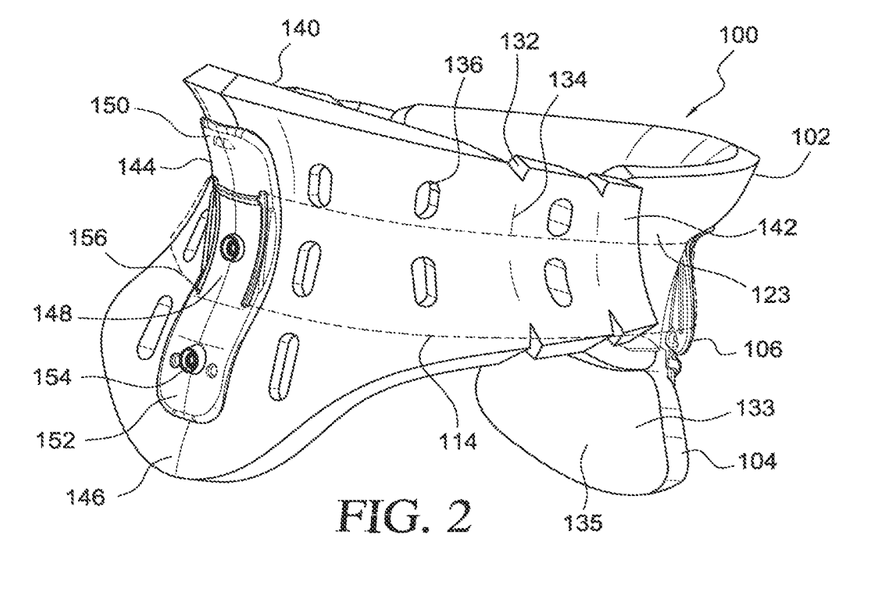
FIG. 2 is a rear perspective view of the cervical collar of FIG. 1.

FIGS. 1 and 2 depict a first embodiment of a cervical collar 100 having a front component 102, and a sternum pad 104 adjustably mounted to the front component 102 by an anterior height adjustment mechanism 106. The height adjustment mechanism 106 has an upper part 108 fixably secured to the front component 102, and a lower part 110 fixably secured to the sternum pad 104. A trachea opening 112 is formed between the upper and lower mechanism parts 108, 110 which are rigid or semi-rigid, thereby providing a rigid or semi-rigid border to the trachea opening. This is particularly advantageous should inspection or airway tubes be applied at the trachea of the wearer.

The front component 102 is arranged to secure to a rear component 140 by a strap system 114 secured to strap loops 122 formed on the upper mechanism part 108, and strap slots 156 connected to the rear component 140.

The front collar has a vein clearance configuration 143 as particularly described in pending U.S. patent application Ser. No. 12/729,536, filed on Mar. 23, 2010, and incorporated herein by reference.

The sternum pad 104 is preferably constructed from a compressible and flexible foam or a similar material of any type described herein. The lower mechanism part 110 defines a central tab 116 which may be connected to the remainder of the lower mechanism part 110 via a central living hinge 118 so as to accommodate the movement and anatomy of a wearer of the collar. Side tabs 130 straddle the central tab 116 and are spaced from the central tab 130 by a clearance 138. The side tabs 130 may optionally include a living hinge 182 to likewise accommodate movement and anatomy of a wearer. The sternum pad 104 may be secured to the lower end of the lower mechanism part 110 via fasteners 120.

Figure 4:
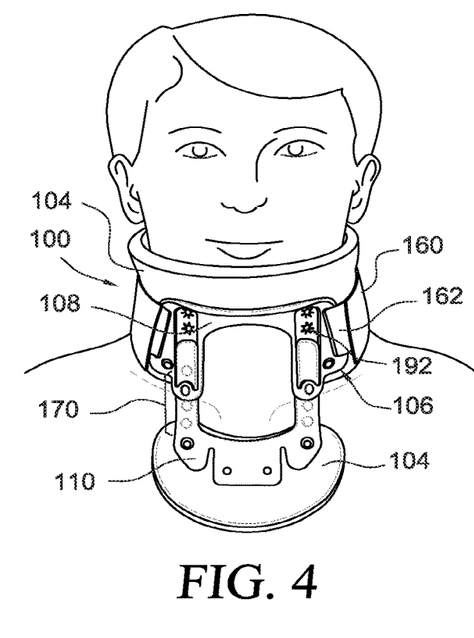
FIG. 4 is a front perspective view showing the cervical collar of FIG. 1 placed on a wearer.

The adjustability of the height adjustment mechanism allows for selective positioning of the sternum pad 104 relative to the front component 102 so that the sternum pad 104 is spaced a height 170 downwardly directed away from the front component 102, as shown in FIG. 4. In order to know the settings of the location of the sternum pad 104 relative to the front component 102, windows 128 are formed on opposed side of the upper mechanism part 108 which encircle or identify indicia 126 indicating certain predetermined heights of the front component 102 relative to the sternum pad 104. The upper mechanism part 108 defines grooves 128 located at opposed sides of the trachea opening 112 and are arranged to accommodate the arms 124 of the lower mechanism part 110.

The rear component 140 has side end portions 142 that preferably outwardly overlap side end portions 141 of the front component 102 which are located on the side portions 121, 123, respectively. While shown in the preferred configuration, the cervical collar can be configured so that the side end portions 141 of the front component outwardly overlap the side end portions 142 of the rear component 140.

As shown in FIGS. 1-5, the front component 102 has a center portion 119 whereupon the height adjustment mechanism 106 is secured and is located between boundaries 137, 139. The front component defines side portions 121, 123 that extend beyond the center portion 119 along the anterior side of the wearer's neck, and are without any reinforcement from the height adjustment mechanism 106. The sternum pad 104 defines side portions 131, 133 extending below and to the side of the height adjustment mechanism 106, and also defines a lower portion 135 that extends beyond and below the height adjustment mechanism 106 along a wearer's sternum. The side portions 131, 133 and lower portion 135 are without any reinforcement from the height adjustment mechanism 106. The front component defines a chin portion 145 bulging outwardly relative to the height adjustment mechanism 106, and only reinforced along its underside by the chin portion 164 of the height adjustment mechanism 106.

A posterior reinforcement support 144 is secured along a midline 146 of the rear component 140. The reinforcement support 144 defines a middle section 148, an uppermost section 150 and a lowermost section 152. The middle section 148 and the lowermost section 152 are preferably mounted flush to the rear component 140. The uppermost section 150 protrudes outwardly from the rear component 140 so as to form a gap 158 therebetween. The gap 158 allows for a slight expansion of the rear component 140 relative to the reinforcement support 144 so as to accommodate additional sizing of the wearer's neck. The middle and lowermost sections 150, 152 however are adapted to firmly restrain the wearer's spine regardless of any additional sizing of the wearer's neck, particularly since the fasteners are located along these sections of the reinforcement support.

The reinforcement support 144 is secured to the rear component 140 via a plurality of fasteners 154, and the strap system 114 secures to the rear component 140 by slots 156 formed by the reinforcement support 144. The reinforcement support is configured to have a cervical arch support so as to maintain neutral alignment of the cervical spine.

The rear component 140 has a pattern of openings 136 extending through the thickness of the rear component to provide for a circulation of air between the wearer and outside of the cervical collar, thereby reducing heat and moisture for the wearer due to wearing the collar. According to this embodiment, the rear component includes a series of notches 132 located at opposed end portions of upper and lower sections of the front component. At least one elongate opening 134 is defined between each set of upper and lower notches 132 to facilitate removing a section of the front component in order to reduce the width of the collar. The opening 134 may extend in part through the front component or extend through the entirety of the front component.

Figure 3:
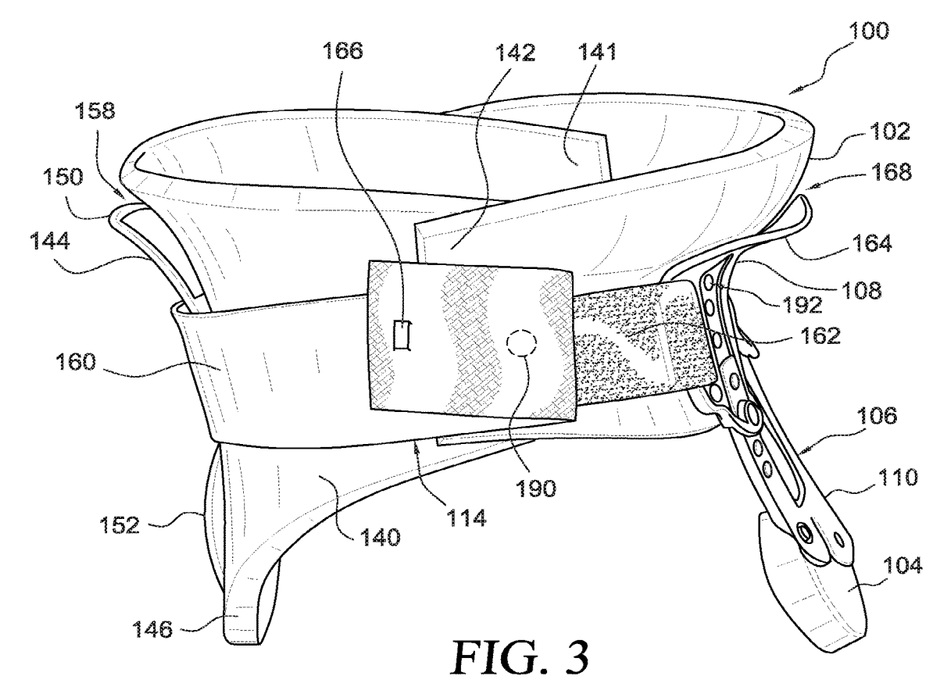
FIG. 3 is a side view of the cervical collar embodiment of FIG. 1 showing a portion of the strap drawn back.

In reference to FIG. 3, the strap system 114 forms an adjustable bilateral hook and loop system to ensure proper fit. The strap system includes a strap 160 extending around the rear component 140 (through the slots 156 of the reinforcement support 144) and over the side end portions 141, and is securable to straps 162 mounted to the side end portions 142 of the front component 102. The strap 160 preferably has a loop material. The straps 162 preferably have a hook material engageable with the loop material of the strap 160, and are mounted to the front component 102 via fasteners 190. The end portion of the strap 160 includes a tab 166 which allows for the clinician to quickly mate the straps 160, 162 so as to efficiently immobilize the neck of the wearer.

The upper part 108 of the height adjustment mechanism 110 defines a chin portion 164 generally protruding outwardly from the front component 102 so as to form a gap 168. The gap 168 is variable in that the wearer can adjust the chin slightly while the neck is immobilized. There are preferably no fasteners mounted near the uppermost portion of the upper part, thereby allowing for some adjustability for the wearer of the collar. It will be noted that the chin portion 164, as with the remainder of the height adjustment mechanism, is substantially rigid, therefore the variability of the gap is due at least in part to the compressibility and flexibility of the front component relative to the chin portion.

Figure 5:
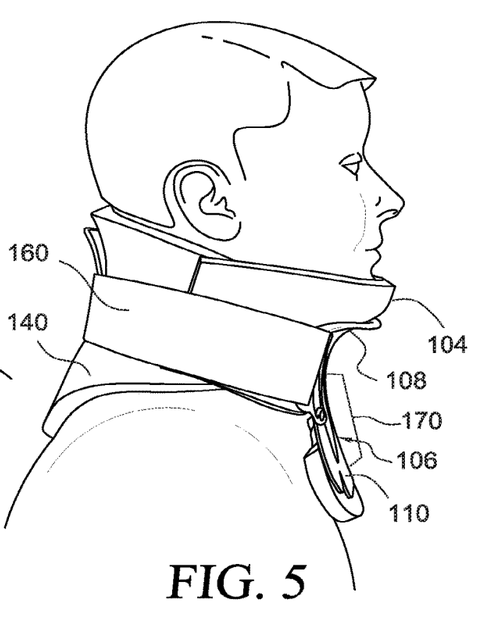
FIG. 5 is a side perspective view showing the cervical collar of FIG. 1 placed on a wearer.

As shown in FIGS. 4 and 5, the height adjustment mechanism 106 permits height adjustment 106 of the front component 102 relative to the sternum pad 104 over a range of heights 170 of the sternum pad 104 from the front component 102 to thereby form a range of sizes to the trachea opening. This height adjustment allows for the cervical collar to be provided in a "one-size-fits-all" format, and permits the clinician to quickly immobilize the wearer's neck. The clinician can also reduce inventory cost without compromising the safety of cervical immobilization collar for the wearer. The height adjustment mechanism enables customization for individual requirements while not requiring an abundance of collars in stock.

Figure 6:
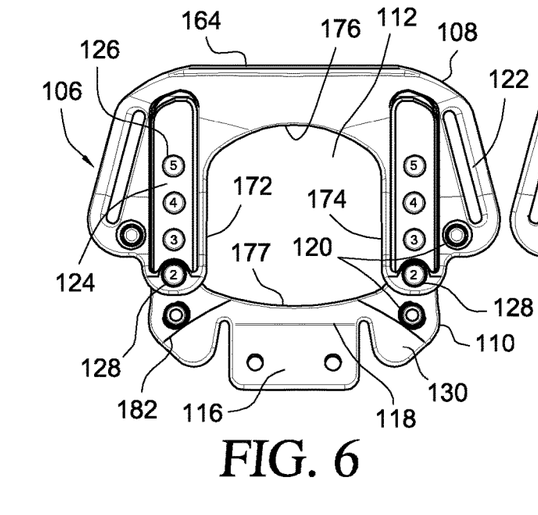
FIG. 6 is a front elevational view of a height adjustment mechanism embodiment.
Figure 7:
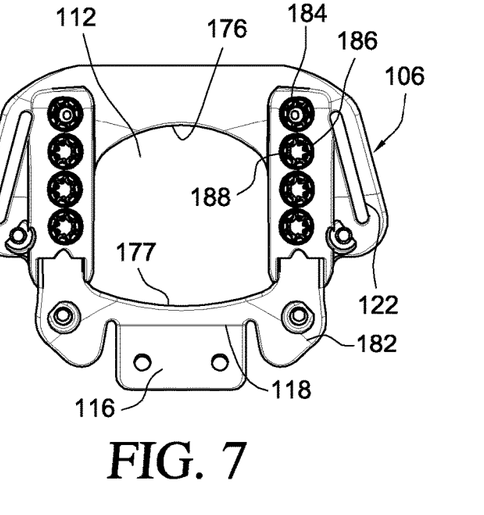
FIG. 7 is a rear elevational view of the height adjustment mechanism embodiment of FIG. 6.
Figure 8:
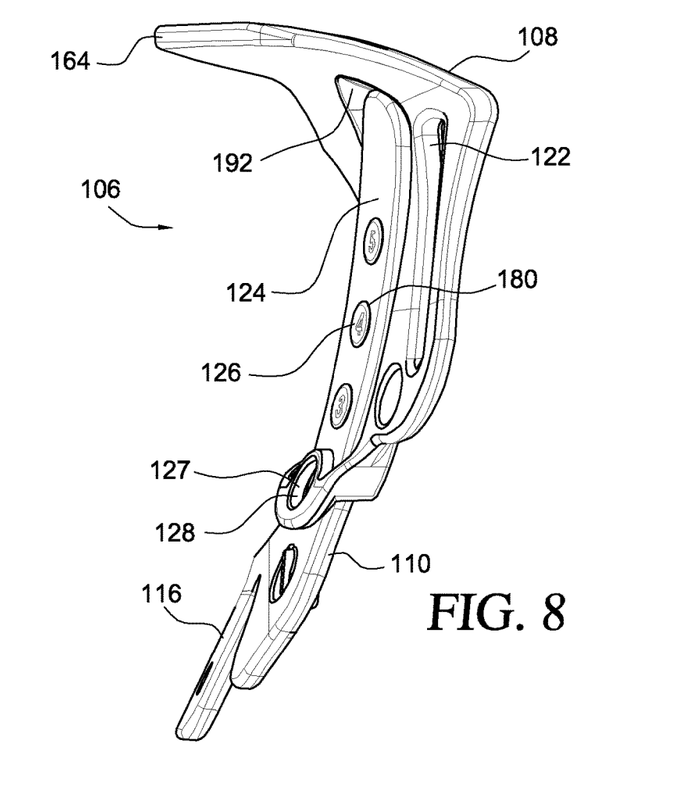
FIG. 8 is a side elevational view of the height adjustment mechanism embodiment of FIG. 6.

FIGS. 6-8 illustrate a preferred embodiment of the height adjustment mechanism 106, in greater scale than shown in FIG. 1. Particularly, the arms 124 of the upper part 108 each define indicia 126 along their height. A lip 180 is provided around each indicia 126, and the lip 180 is configured in shape to be snugly received by the contours of the window 128 formed on the lower part 110. The lip thereby allows for serving as a guide prior to permanently locking the arms to the upper part since they indicia corresponds to locking elements.

Each window is formed by a retainer 127 belonging to the upper part 108. The retainers 127 allow for the arms of the lower part to be inserted therethrough such that the arms extend past the retainers 127 and into an elongate and open recess 192 of the upper part. The recess 192 is arranged to receive a rear surface of the arm, whereas a front surface of the first arm is exposed above the first retainer. The retainer is preferably located at a bottom portion of the upper part, such that when the arm is inserted through the retainer, the arm extends past the retainer and toward a top portion of the upper part.

The upper and lower parts 108, 110 form a border to the trachea opening 112 of the cervical collar. Specifically, the upper part 108 defines the uppermost arch 176 and size portions 172, 174 of the trachea opening 112, while an uppermost arch 177 of the lower part forms the lowermost arch of the trachea opening 112. The combination of these portions of the upper and lower parts allows for the trachea opening to be maintained regardless of the height adjustment of the collar.

Each of the arms 124 defines a pin 184 that extends inwardly toward the front component and is fixedly securable to at least one of a series of locking elements 186 formed along the upper part. Each of the locking elements 186 includes a plurality of fingers 188 which securely and lockingly engage the pin so that the pin 188 cannot be withdrawn from the locking element 186 once it is pressed thereinto.

As shown in FIG. 8, the arm 124 has a curvature that is not exactly parallel to a curvature of the upper part 108. This lack of a parallel relationship among the arm and the curvature, hence the recess 192 on the upper part, results in a variable gap between portions of the arm and the recess 192. By forming the arm 124 so that it is not exactly parallel to the upper part 108, the height adjustment mechanism is strengthened by minimizing the possibility of the height adjustment mechanism at bending as well as forming a better fit when the pin is locked into the locking elements.

In accordance with the embodiments described herein, the front and rear components, as well as the sternum pad are preferably constructed from PLASTAZOTE or similar foam material. PLASTAZOTE itself is well known in the art of cervical collars, and is distinguished as being compressible and flexible. Specifically, PLASTAZOTE is a polyethylene foam and is considered as having excellent cushioning properties, thereby rendering the front and rear components and the sternum pad as compressible and flexible. In accordance with the embodiments shown herein, the front and rear components conform to the shoulder, and the front component has a mandible contour allowing for superior stability and comfort.

In the embodiments herein, the strap system is provided in combination with the compressible foam based front and rear components to provide sufficient support to immobilize the neck of the wearer. Specifically, the arrangement of the front and rear components restricts cervical spine flexion, extension and rotation to promote patient recovery. Moreover the use of PLASTAZOTE allows for the front and rear components to be latex-free, non-toxic and hypoallergenic.

The height adjustment mechanism and the reinforcement support are substantially rigid components, particularly provided to limit movement of the wearer's neck. The two piece design of the front and rear components enhance patient comfort and compress and flex about the wearer's neck whereas the rigid height adjustment mechanism and reinforcement support remain rigid when worn by the wearer, and when the strap system is tensioned about the neck of the wearer.

Of particular note, while the height adjustment mechanism allows for an adjustment in height of the collar, the height adjustment mechanism remains rigid so as to provide anterior support for the user. The height adjustment mechanism borders the trachea opening thereby providing a substantially rigid border about the trachea opening. This allows for a large trachea opening, regardless of the height setting, and permits for quick access to the carotid pulse monitoring and emergency tracheotomies. It will also be noted that the variable gap between the gap between the chin portion of the height adjustment mechanism and the front component makes the cervical collar maneuverable for assisting in airway management of the cervical collar for the wearer.

According to this embodiment, the locking of the height adjustment mechanism is arranged to be permanently locked at one of the predetermined heights defined by the indicia so that the wearer cannot change the height setting once it has been locked. The benefit of this embodiment is that the height adjustment mechanism is more secure, with less risk of accidentally unlocking it. There is also a reduction in the risk that of the patient changing the setting. However, the embodiments herein are not to be limited to permanent locking elements, and it is within the scope of the invention to make the locking elements adjustable and not permanent.

Figure 9:
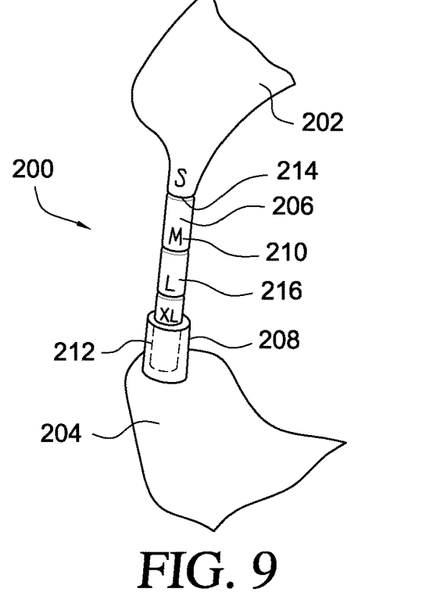
FIG. 9 is a perspective view showing another height adjustment mechanism embodiment.

FIG. 9 depicts another embodiment of a height adjustment mechanism 200. In this embodiment, the adjustment mechanism 200 has top and bottom parts 202, 204, wherein a rod 206 extends from the top part 202 into a receptacle 208 having a fitting contour 212 located on the bottom part 204. The rod 206 defines a plurality of breaks 214 having indicia 216 which correspond to different height sizes.

In operation, the rod 206 is provided in the largest configuration, as exemplified by "XL." Should the wearer have a shorter height, the break according to the wearer's size is snapped so that the rod 206 is reduced in height and inserted into the receptacle 208. The fitting contour 212 is configured in a manner such that there is a frictional fit with the lowermost end of the rod 206 when inserted therein.

Figure 10:
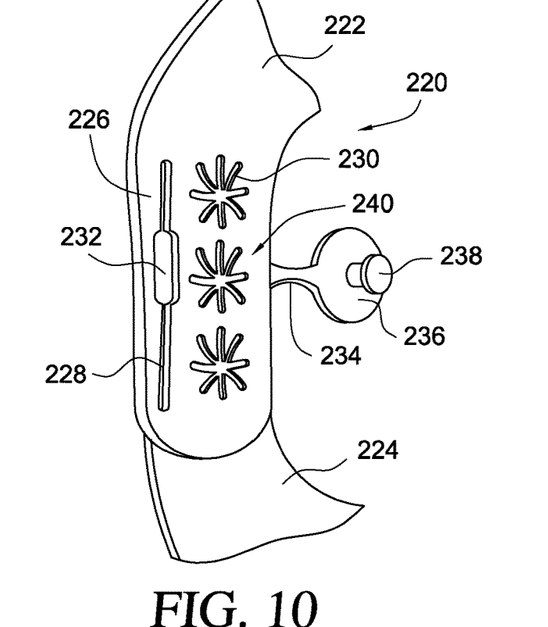
FIG. 10 is a perspective view showing yet another height adjustment mechanism embodiment.

FIG. 10 exemplifies yet another adjustment mechanism 220 having top and bottom parts 222, 224, wherein an end portion 226 extends over the bottom part 224. The end portion 226 defines an elongate slot 228 and a plurality of locking recesses 230 generally arranged along the slot 228. The slot 228 may be provided with detents which correspond to the locking recesses.

The bottom part 224 includes a slider 232 which extends through and engages the slot 228, and an arm 94 laterally extending from a side of the bottom part 224 and generally in alignment with the slider 232. The arm 234 carries a head 236 having a fastening element 238, such as a rivet or a locking pin, which is adapted to engage one of the locking recesses 230. The locking recesses 230 are arranged in a pattern which corresponds to different height settings of the collar.

In operation, the caregiver moves the slider in the slot so that it is aligned with one of the locking recesses. Once aligned at the proper setting, the arm is turned over the edge of the top and bottom parts. The fastening element is then pressed into the locking recesses whereat it engages and effectively maintains the desired collar height.

The fastening element may be arranged to permanently lock into one of the locking recesses. By permanently locking, the collar cannot be tampered with by the wearer, the tampering of which can result in improper alignment and lack of immobilization for the wearer.

Of course, a variety of other adjustment mechanisms are available, and the adjustment mechanism can be modified in a manner to accommodate such other adjustment mechanisms.

Figure 11:
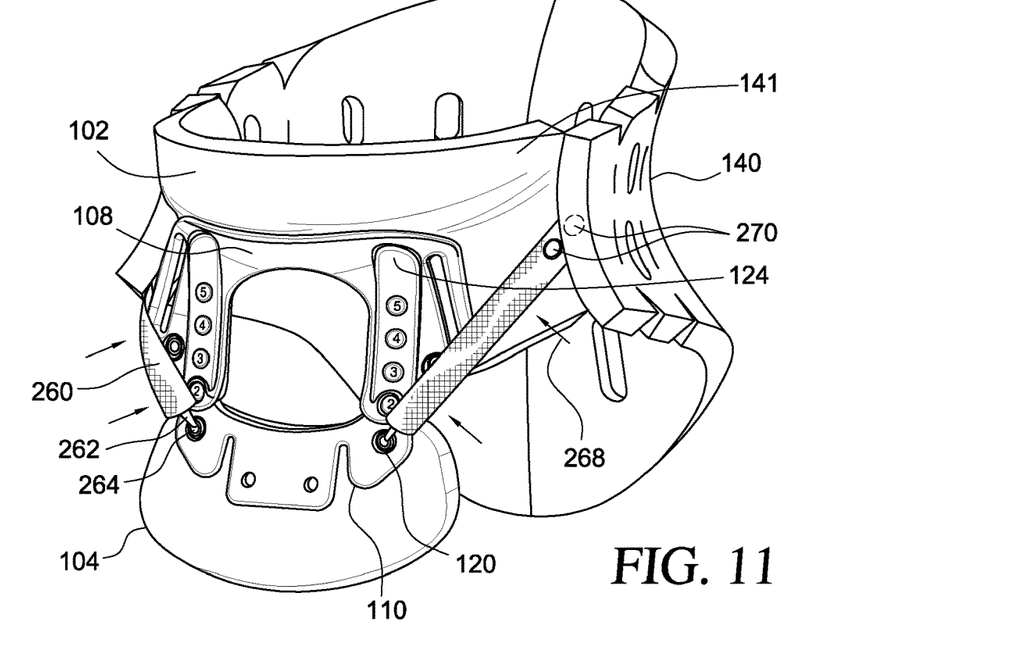
FIG. 11 is a perspective view of another cervical collar embodiment.

FIG. 11 depicts another embodiment of the cervical collar including tightening bands 260 used to stabilize the arms 124 against the upper part 108 by connecting between the lower part 110 on the sternum pad 104 and the side end portions 141 of the front component 102. The tightening bands 260 secure at a first end 270 to the front component side end portions 141, either behind the side portions 142 of the rear component 140, or forward the side end portions 142. The tightening bands 260 secure at a second end 264 to the fasteners 120. The tightening bands 260 are preferably removable at both the first and second ends.

The tightening bands stabilize the height adjustment mechanism such that when the collar is set in the lowest setting, the tightening bands are loose. When the height adjustment mechanism is in its tallest setting, the tightening bands are fully stretched and maintain the sternum pad in place against the wearer by urging forces 268 against the wearer.

Figures 12, 13:
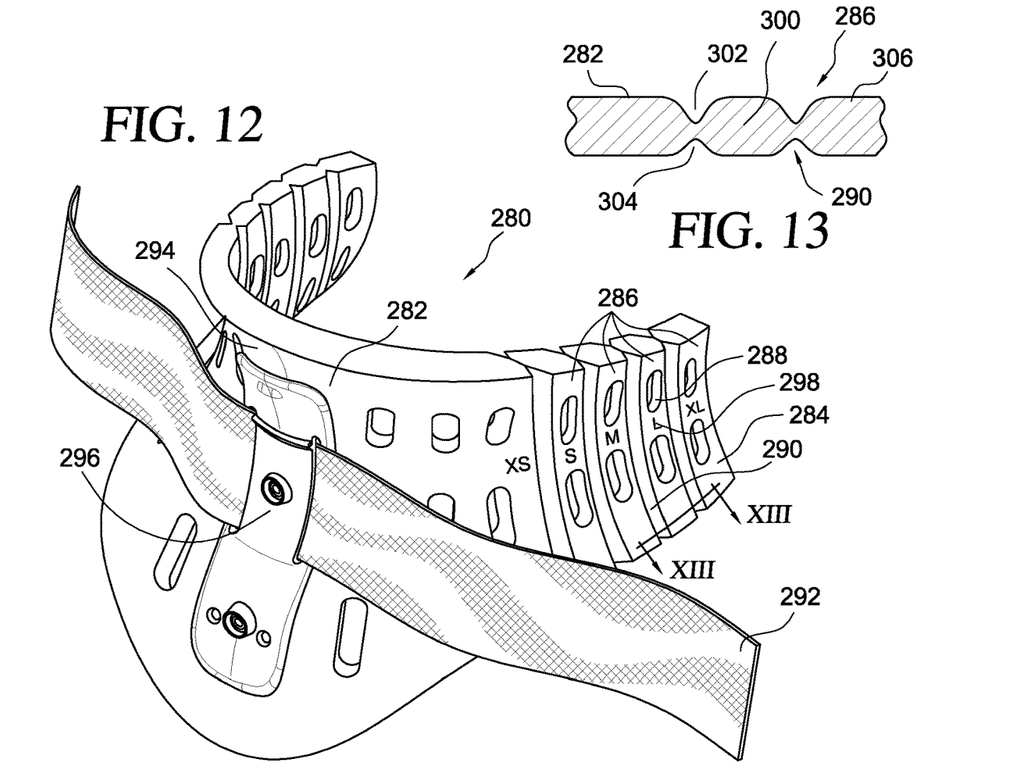
FIG. 12 is a perspective of another rear component embodiment of the cervical collar.
FIG. 13 is a sectional view taken along line XIII-XIII in FIG. 12.

FIG. 12 illustrates another embodiment of the rear component 280 of the cervical collar. According to this embodiment, the rear component 280 includes a base rear portion 282 having side portions 284 extending therefrom. A reinforcement support 296 is provided on the rear surface of the rear component 280, and may be arranged similarly as depicted in FIG. 2.

Each of the side portions 284 has breakaway sections 286 corresponding to different lengths of the side portions 284. Removal of the breakaway sections 286 allow for the clinician to easily reduce the circumference of the rear component and hence the cervical collar. The breakaway sections 286 are delimited by areas of reduced thickness 290 at which locations the breakaway sections 286 are configured to be torn away from the base rear portion 282 according to a certain circumferential size of the wearer.

As an alternative to the areas of reduced thickness, the breakaway sections may be delimited by a line of perforations such that these perforations comprises a plurality of thin holes that permit easy tearing of the breakaway sections from the base rear portion.

The rear component 280 includes a plurality of openings 288 to provide ventilation to the wearer. Of particular note, certain of the openings 288 outside of the rear portion 282 may be confined within the breakaway sections 286 themselves so as to avoid uneven edges of the rear component 100.

FIG. 13 exemplifies a configuration of how the breakaway sections 286 are constructed. In this example, the areas of reduced thickness 290 include notches 302, 304 extending along the entire height of the inner and outer sides of the rear component 280. While the notches 302, 304 result in reducing the thickness of the side portions 284, they provide a thickness that allows for tearing away from the rear portion 282, but still enable functionality of the side portions when the corresponding breakaway sections 300, 306 (and so forth) are not removed from the rear portion.

Other configurations are available for constructing the breakaway sections which would be understood by the skilled person. It will be noted that the notched sections can have a thickness which withstand tearing, and instead, they merely serve as areas which facilitate the cutting of the side portions to accommodate a specific wearer's size.

Aside from the breakaway sections which are depicted as being adapted to adjust the circumference of the collar, other breakaway sections may be provided to modify the collar for different medical indications. For example, it has been found that the rear of the collar does not necessarily require adjustment in height. However, for patients that only require support for flexion, lowering the support in the back would increase breathability and comfort to the wearer.

In addition to the breakaway sections, the collar can be provided with a plurality of inserts for each of the openings. These inserts are arranged, including the configuration of reduced thickness, perforations or other means known to the skilled person, for easy detachment from the collar. Prior to adjustment, the collar has these openings filled with the inserts and the caregiver can adapt the collar by removing these inserts so that certain area have greater ventilation than other areas according to the demands of the wearer.

Figure 14:
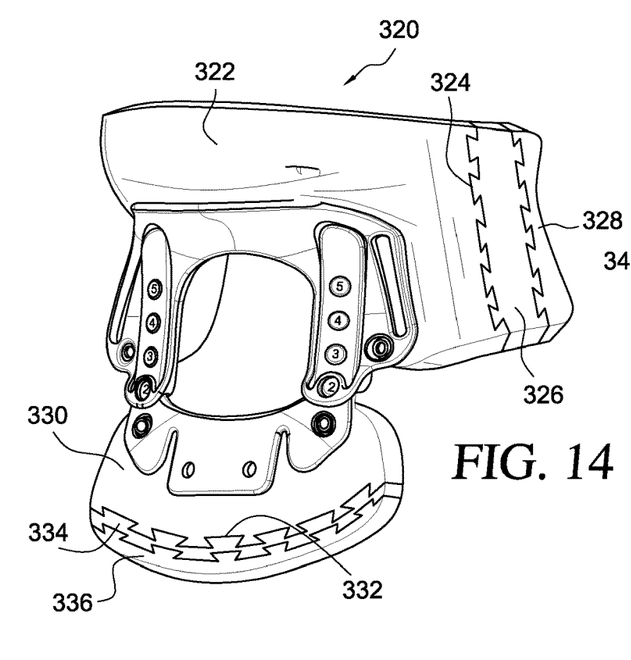
FIG. 14 is a perspective view of a front component embodiment of a cervical collar.

Turning to the embodiment 320 of FIG. 14, the front component 322 can have width adjustment by the use of removable segments 326, 328 on opposed end portions of the front component. The removable segments 326, 328 are secured to the front component by an interlocking profile 324 formed along at least one of the vertical peripheries of the removable segments. Opposed vertical peripheries of either the front component itself 322 or the removable segments 326, 328 are precut with the interlocking profile 324 so that the opposed vertical peripheries interlock.

Because the interlocking removable segments are precut, they are readily separable from the front component and will include generally clean lines demarcating a portion of the periphery of the front component. The interlocking profile is preferably of a low profile allowing for interlocking of the parts, while minimizing contours of the interlocking profile so as to avoid a substantially jagged profile.

Figure 15:
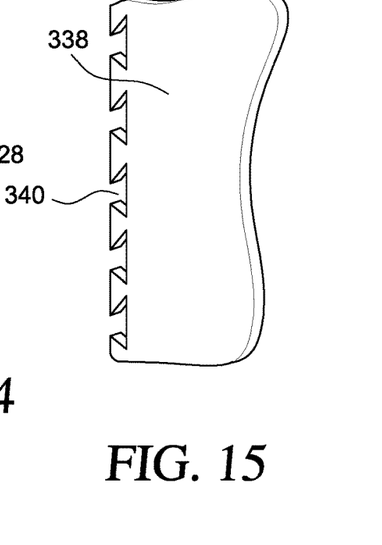
FIG. 15 is a perspective view of a breakaway section from the front component embodiment of FIG. 14.

If it is desired to reduce the width of the collar, then one may pull apart the desired removable segment to form the new width of the front component. If in the event it is desired to add width to the collar, one may place the removed segment to the front component, or in the alternative, an extension segment 338 having an interlocking profile 340, as shown in FIG. 15, may be added to the front component. The extension segment 338 has a greater width than the removable segments 326, 328 and may be placed together with the removable segments or alone on the front component.

The sternum pad 330 may include removable segments 334, 336 having interlocking profiles 332 which are adapted to be added to or removed from the sternum pad. The embodiment in FIG. 14 shows by way of example how any of the foam components of the collar, whether the front component or the rear component, and the sternum pad may be arranged to have width and height adjustment from interlocking, removable segments. The front and rear components and the sternum pad may have either the width or height adjustment with interlocking removable segments, or may include both width and height adjustment with interlocking removable segments.

Figure 16:
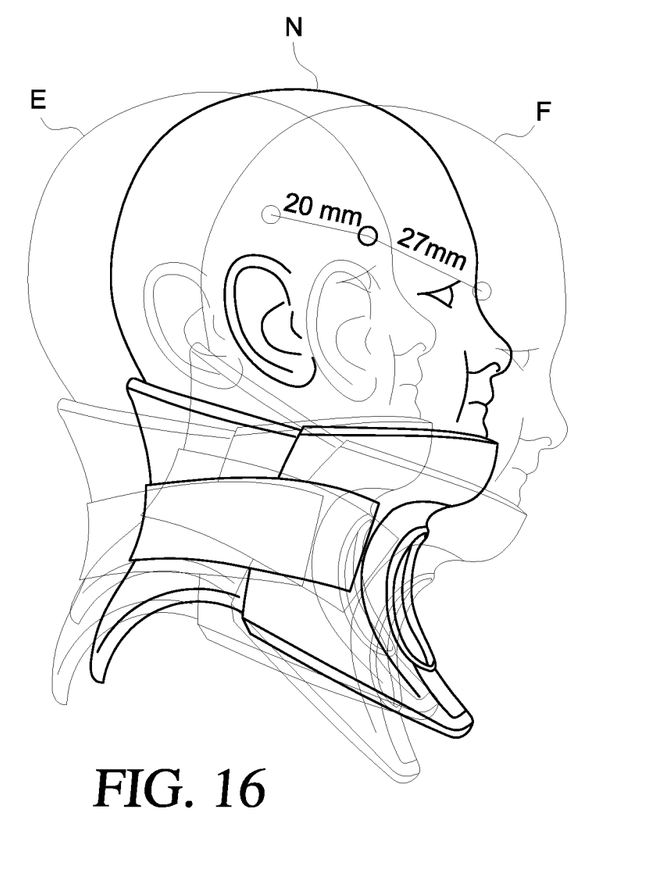
FIG. 16 is a perspective view exemplifying immobilization of a prior art cervical collar without height adjustment on a wearer.
Figure 17:
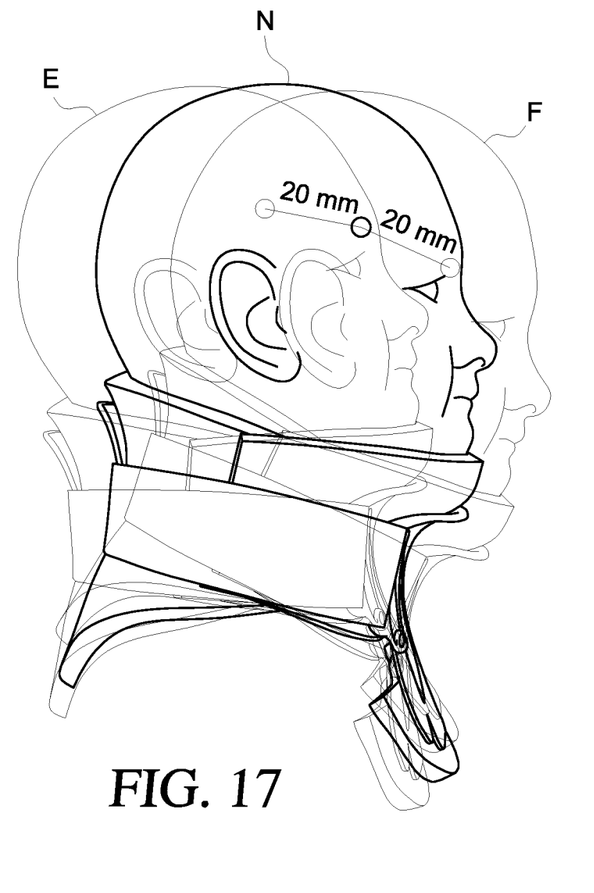
FIG. 17 is a perspective view showing immobilization of the cervical collar according to FIG. 1 having height adjustment on a wearer.

FIGS. 16 and 17 depict the motion restriction obtained by known cervical collars in comparison to the adjustable cervical collar of the invention. In the example depicted in FIG. 16, a well known collar named the Philadelphia Tracheotomy Collar and sold by Ossur hf is shown to have motion restriction of the nodding motions of the neck whereas for flexion F (bending the neck toward the chest) the distance is about 27 mm, and for extension E (bending the neck back) the distance is about 20 mm from a neutral position N.

By properly sizing the cervical collar using the height adjustment mechanism and sternum pad described herein, FIG. 17 shows the cervical collar of the invention as having a motion restriction of about 20 mm for flexion F, and about 20 mm for extension E from a neutral position N. The height adjustment mechanism of the cervical collar in FIG. 17 thereby allows the clinician to assure that the collar tightly immobilizes the wearer's neck, and particularly allows for superior immobilization for extension.

It is particularly advantageous for a cervical collar to have excellent motion restriction so as to limit or prevent cervical pain, protect spinal instability, and protect the cervical spine in emergency situations. Cervical collars have also been found to provide benefits of proprioception and decreased loading to injured muscles or ligaments by increased support to the region. Moreover, it is likely that those cervical collars have the benefit of increasing local temperature of the soft tissue surrounding the cervical region by reducing heat loss and providing a placebo effect.

By having the ability to tailor the size of the collar both circumferentially and by height, and further including means for ventilating the collar and reducing foam size (such as by only including a sternum pad), the cervical collar of the invention allows for improved pain relief, immobilization, restraint against extreme neck motions, and rest of soft tissue surrounding the neck.

While the foregoing embodiments have been described and shown, it is understood that alternatives and modifications of these embodiments, such as those suggested by others, may be made to fall within the scope of the invention. Moreover, any of the principles described herein may be extended to any other orthopedic devices.

The invention claimed is:

1. A cervical collar having an adjustable height, comprising:
a front component defining an upper portion of a tracheal opening located within a center portion of the front component and side portions extending from opposed sides of the center portion;
a sternum pad bordering a lower portion of the tracheal opening; and
a height adjustment mechanism directly secured to the front component at only the center portion of the front component, the height adjustment mechanism selectively connecting the front component to the sternum pad at a permanently locked position among a plurality of predefined distances along an adjustable length located between the front component and the sternum pad and forming part of the adjustable height of the cervical collar;
wherein the height adjustment mechanism includes:
an upper part secured to the front component and bordering the upper portion of the tracheal opening, the upper part defines a chin portion protruding outwardly from the front component so as to form a variable gap; and
a lower part directly secured to the sternum pad, the lower part defining a central tab having a living hinge.

2. The cervical collar of claim 1, wherein the height adjustment mechanism forms a rigid border about the tracheal opening.

3. The cervical collar of claim 2, wherein the front component is formed from a compressible material.

4. The cervical collar of claim 1, wherein the side portions are flexible relative to the height adjustment mechanism.

5. The cervical collar of claim 1, wherein the lower part defines side tabs straddling the central tab, the side tabs spaced apart from the central tab by a clearance.

6. The cervical collar of claim 5, wherein the sternum pad is secured to the lower part of the height adjustment mechanism by fasteners at the side tabs.

7. The cervical collar of claim 1, wherein no fasteners are mounted near an uppermost portion of the upper part defining the chin portion.

8. The cervical collar of claim 1, wherein the lower part of the height adjustment mechanism defines first and second arms bordering opposite sides of the tracheal opening, the upper part defining first and second retainers through which the first and second arms slide, respectively.

9. The cervical collar of claim 8, wherein the upper part defines first and second recesses formed as being elongate and open above the first and second retainers, respectively, which are located at a bottom portion of the upper part and are arranged to surround the first and second arms, the first and second recesses are arranged to receive a rear surface of the first and second arms, whereas a front surface of the first and second arms is exposed above the first and second retainers, respectively.

10. The cervical collar according to claim 9, wherein the first retainer forms a window, the first arm forms a series of location identifiers representing a plurality of distance settings of the front component relative to the sternum pad and corresponding to the plurality of predefined distances, an individual one of the series of location identifiers arranged to be placed in register with the window when the first arm is inserted into the first retainer.

11. The cervical collar according to claim 9, wherein the first retainer is only located at the bottom portion of the upper part, such that when inserted through the first retainer, the first arm extends past the first retainer and toward a top portion of the upper part.

12. The cervical collar according to claim 8, wherein the upper part forms a first recess which is elongate and open, and arranged to accommodate a rear surface of the first arm and a front surface of the first arm extends outside the first recess.

13. The cervical collar according to claim 1, wherein the lower part of the height adjustment mechanism includes a pin fixedly securable to at least one of a series of locking elements formed along the upper part.

14. The cervical collar according to claim 1, further comprising a rear component connecting to the front component, the rear component having a plurality of breakaway sections arranged to be removed without the benefit of a tool, wherein removal of one of the plurality of breakaway sections reduces a circumference of the cervical collar formed by the front component and the rear component.

15. The cervical collar according to claim 1, further comprising a rear component formed from a compressible foam and connecting to the front component, the rear component including a reinforcement support arranged to support a wearer's spine and an elongate strap arranged to secure to the front component.

16. The cervical collar according to claim 1, wherein the sternum pad has side portions extending below and to the side of the height adjustment mechanism, and defines a lower portion extending beyond and below the height adjustment mechanism, the side portions and the lower portion of the sternum pad are located outside of the height adjustment mechanism.

17. The cervical collar according to claim 1, wherein the sternum pad has a width that is narrower in size than a width of the front component.

18. The cervical collar according to claim 1, wherein the height adjustment mechanism defines a pair of strap loops extending from opposed sides of the height adjustment mechanism, the cervical collar further comprising a pair of straps extending from the pair of strap loops and along the side portions of the front component beyond the center portion of the front component and outside the height adjustment mechanism.

* * * * *